US005552380A

United States Patent [19]

Sprecker et al.

[11] Patent Number: 5,552,380

[45] Date of Patent: Sep. 3, 1996

[54] PERFUME USES OF PHENYL ALKANOL DERIVATIVES

[75] Inventors: Mark A. Sprecker, Sea Bright; Richard A. Weiss, Pine Brook; Marie R. Hanna, Keyport, all of N.J.

[73] Assignee: International Flavors & Fragrances Inc., New York, N.Y.

[21] Appl. No.: 356,504

[22] Filed: Dec. 15, 1994

[51] Int. Cl.[6] .......... A61K 7/46

[52] U.S. Cl. .......... 512/20; 512/21

[58] Field of Search .......... 512/20, 21

[56] References Cited

U.S. PATENT DOCUMENTS 3,952,024 4/1976 Winter et al. .......... 260/347.2

OTHER PUBLICATIONS

Arctander I, "Perfume and Flavor Chemicals (Aroma Chemicals)", vol. I, Monographs 989, 990, 991, 1705 and 1707 (Published 1969).

Arctander II, "Perfume and Flavor Chemicals (Aroma Chemicals)", vol. II, Monographs 2502, 2503, 2512, 2520, 2521, 2588 and 2589 (Published 1969).

*Primary Examiner*—James H. Reamer
*Attorney, Agent, or Firm*—Arthur L. Liberman

[57] ABSTRACT

Described are phenyl alkanol derivatives defined according to the structure:

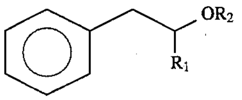

wherein $R_1$ is methyl or ethyl and $R_2$ is hydrogen or acetyl with the proviso that when $R_2$ is hydrogen, $R_1$ is ethyl and when $R_2$ is acetyl, $R_1$ is methyl and uses thereof in augmenting, enhancing or imparting an aroma in or to perfume compositions, colognes and perfumed articles including but not limited to solid or liquid, anionic, cationic, nonionic or zwitterionic detergents, fabric softener compositions, fabric softener articles and hair preparations.

11 Claims, 7 Drawing Sheets

FIG.5
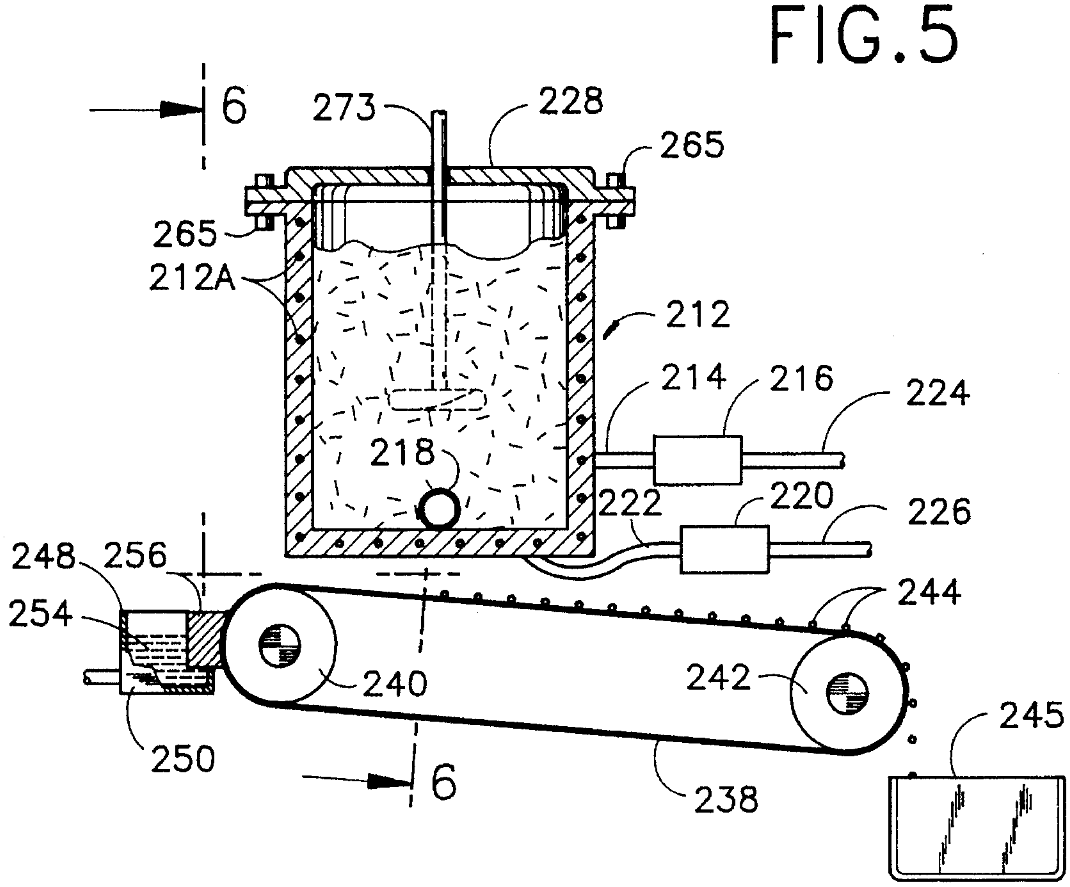
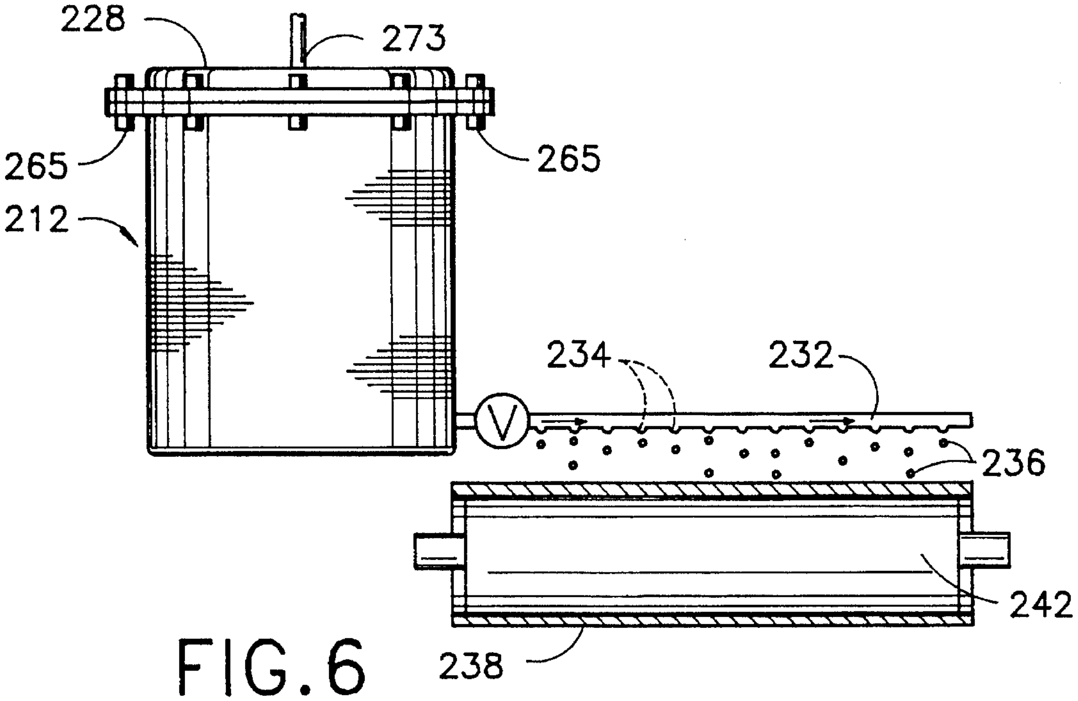
FIG.6

PERFUME USES OF PHENYL ALKANOL DERIVATIVES

BACKGROUND OF THE INVENTION

The instant invention relates to phenyl alkanol derivatives defined according to the structure:

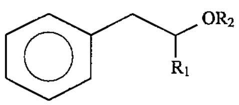

wherein $R_1$ is methyl or ethyl and $R_2$ is hydrogen or acetyl with the proviso that when $R_2$ is hydrogen, $R_1$ is ethyl and when $R_2$ is acetyl, $R_1$ is methyl and uses of same in augmenting, enhancing or imparting an aroma in or to perfume compositions, perfumed articles and colognes.

Inexpensive chemical compounds which are substantive and long-lasting and which can provide strong, persistent herbal, fruity, rose, ozoney, lilac, woody, mimosa, hyacinth, anise, jasmine and honey aromas with sweet, animalic, civet and fresh cut wood undertones are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuous effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Of particular importance are odorants of the muguet type in perfumery as well as the "woody cologne" type in perfumery.

Phenyl alkanols are well known in the art of perfumery. Thus, Arctander "Perfume and Flavor Chemicals" (Aroma Chemicals), Volume I at Monographs 192, 193, 990, 989 and 991 discloses, respectively, the compounds having the structures:

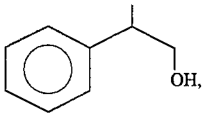

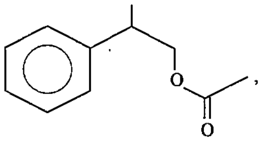

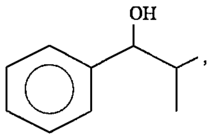

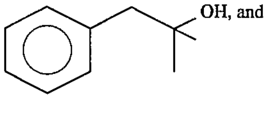

-continued

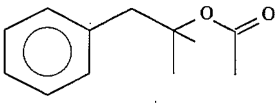

for use in perfumery. Furthermore, Arctander "Perfume and Flavor Chemicals" (Aroma Chemicals), Volume II discloses at Monographs 2512, 2502, 2503, 2520, 2521, 2589 and 2588, respectively, the compounds having the structures:

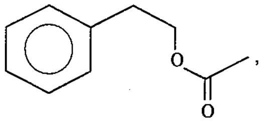

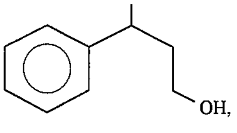

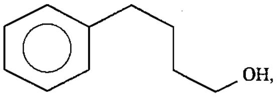

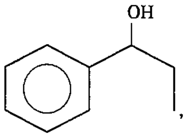

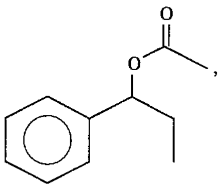

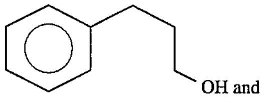

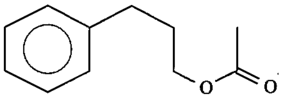

for use in perfumery.

Furthermore, Winter, et al, U.S. Pat. No. 3,952,024 issued on Apr. 20, 1976 (Title: "Furfurylthioacetone") indicates at column 15, line 48 that the compound having the structure:

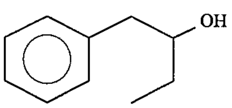

is useful as a food flavor.

Nothing in the prior art, however, infers or discloses the unexpected, unobvious and advantageous fragrance utilities of the compounds having the structures:

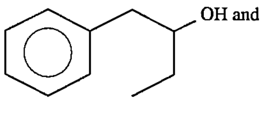

-continued

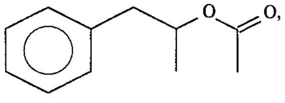

otherwise defined using the generic structure:

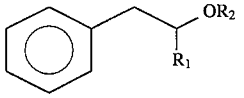

wherein $R_2$ is hydrogen or acetyl and $R_1$ is methyl or ethyl with the proviso that when $R_2$ is hydrogen, $R_1$ is ethyl and when $R_2$ is acetyl, $R_1$ is methyl.

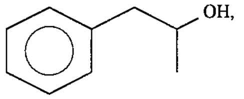

precursor of the compound having the structure:

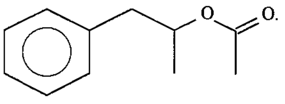

Figure 2:
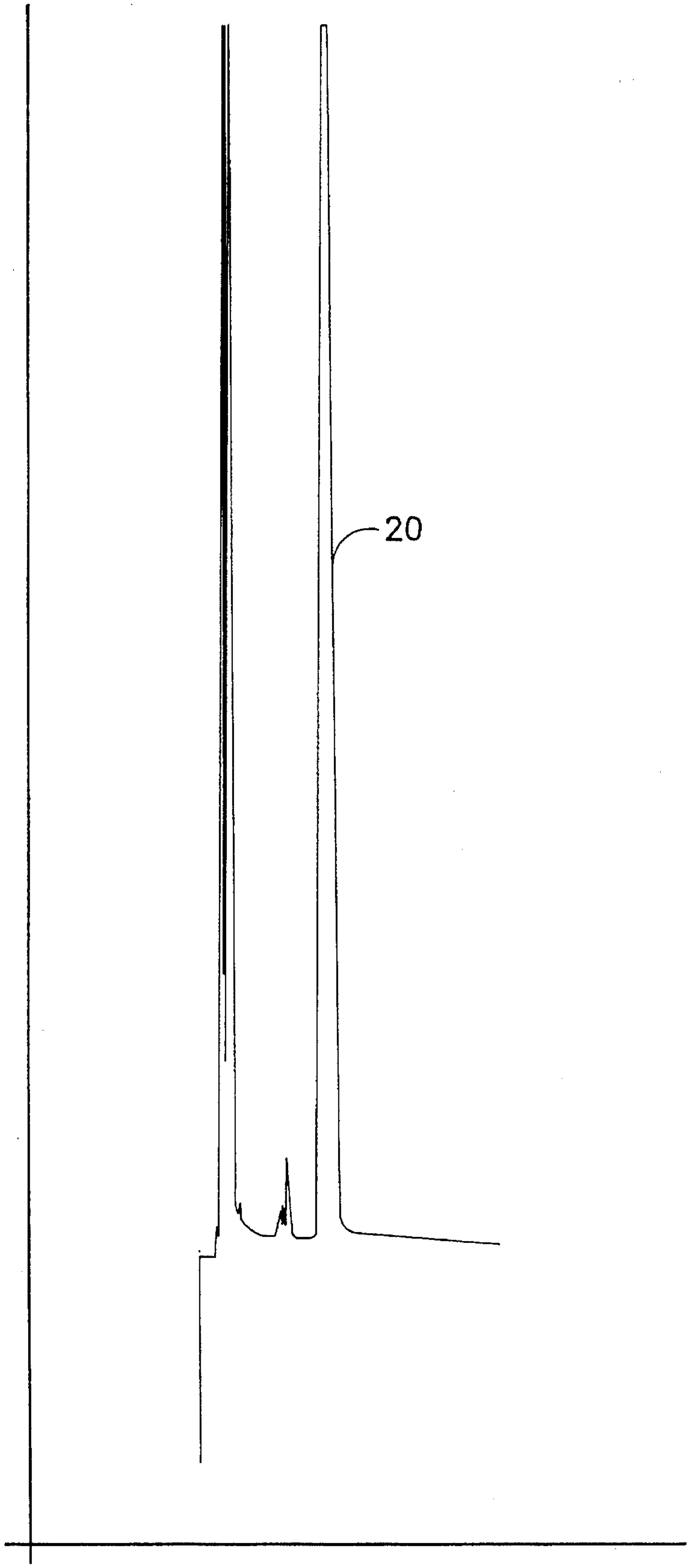

FIG. 2 is the GLC profile for the reaction product of Example I(B) containing the compound having the structure:

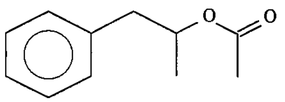

(conditions: SE-30 column programmed at 160° C. isothermal).

Figure 3:
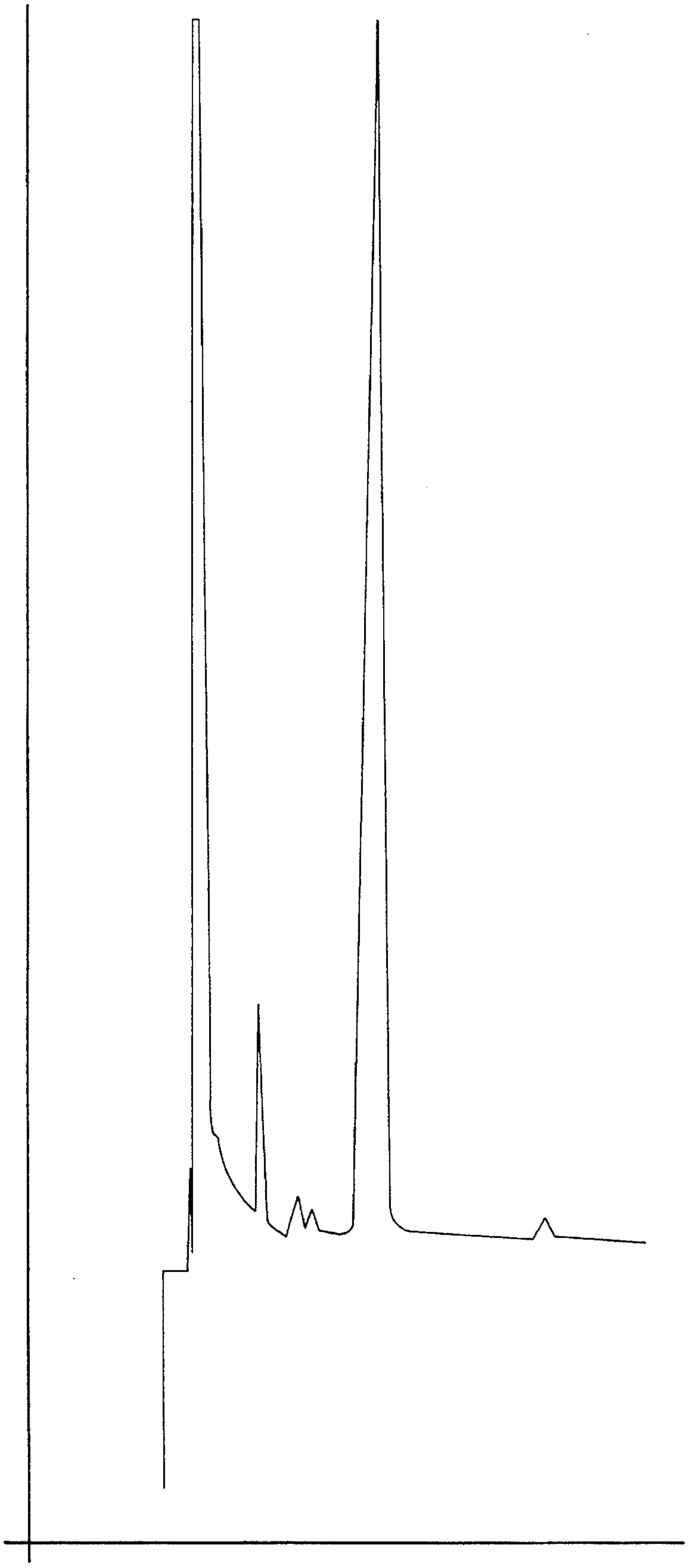

FIG. 3 is the GLC profile for the reaction product of Example II containing the compound having the struture:

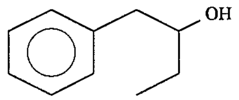

(conditions: SE-30 column programmed at 140° C. isothermal).

Figure 4:
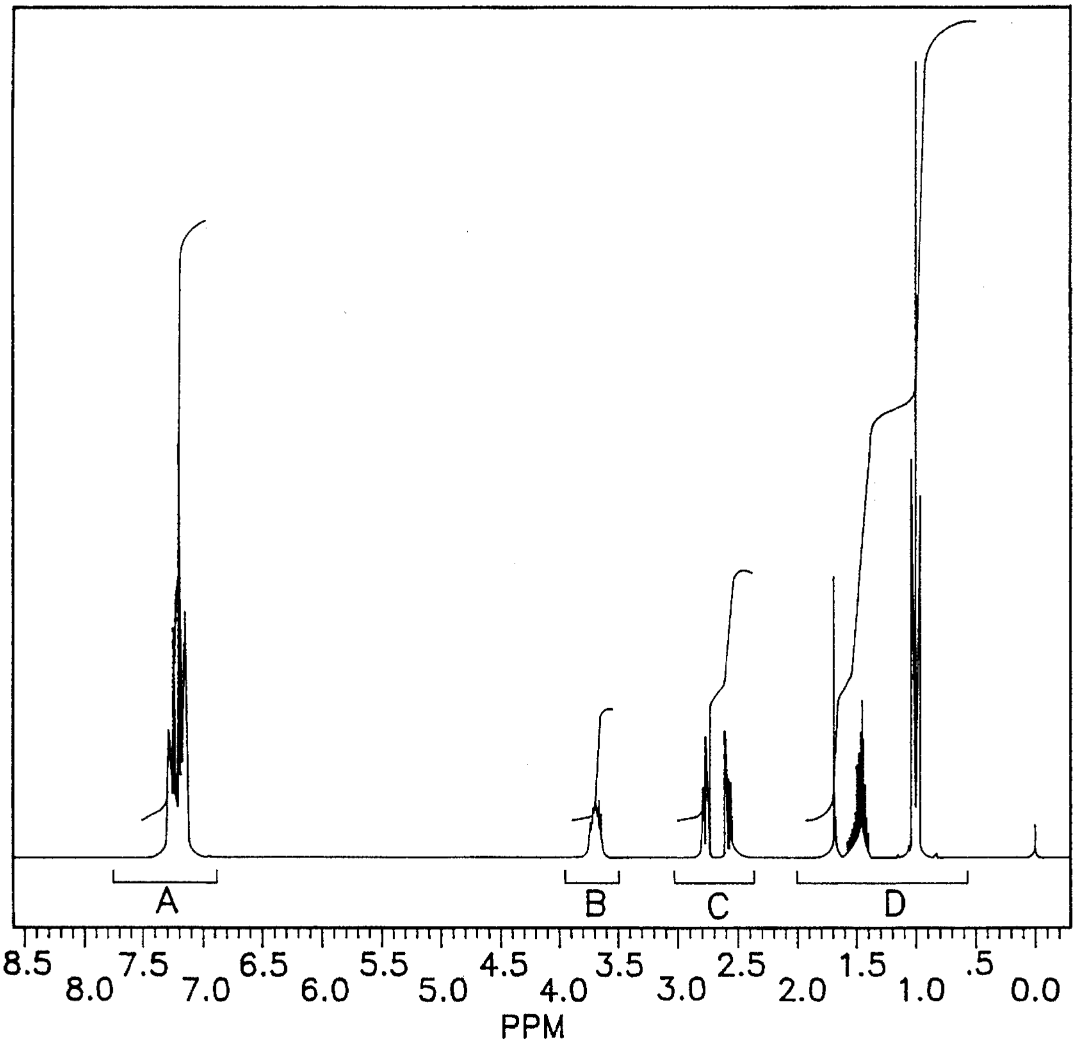
Figure 4A:
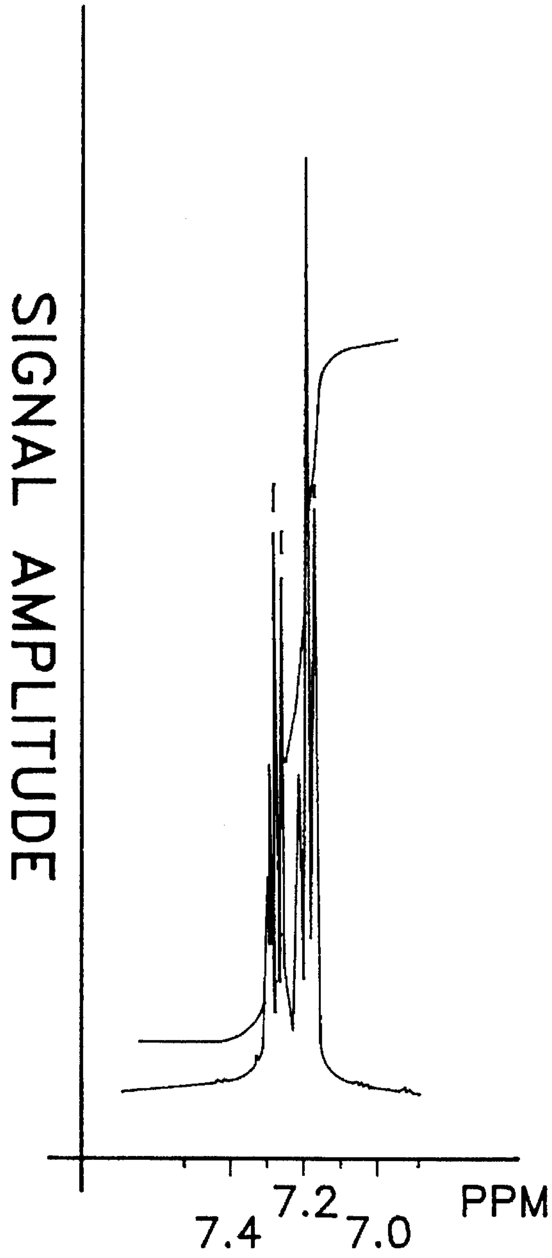
Figure 4B:
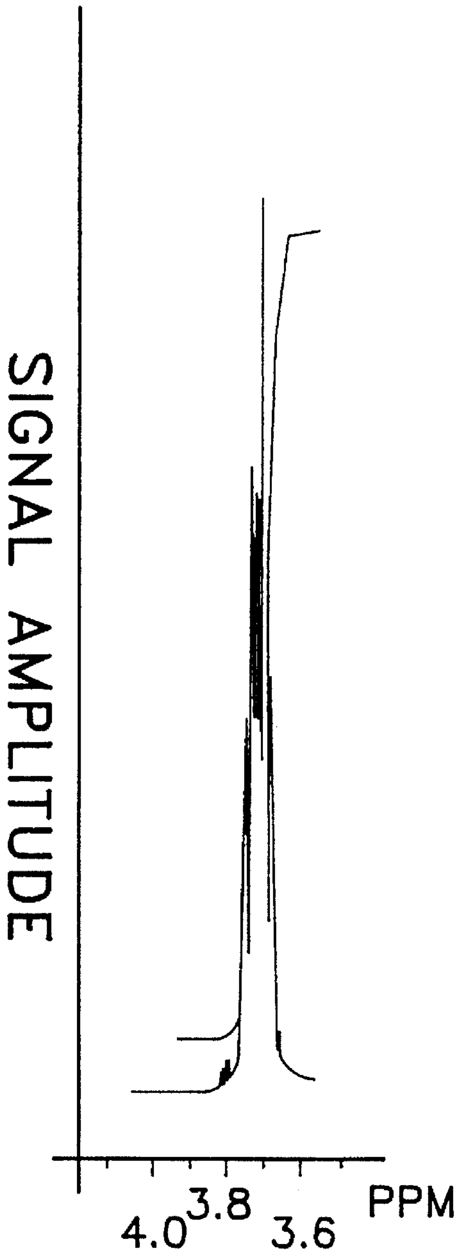
Figure 4C:
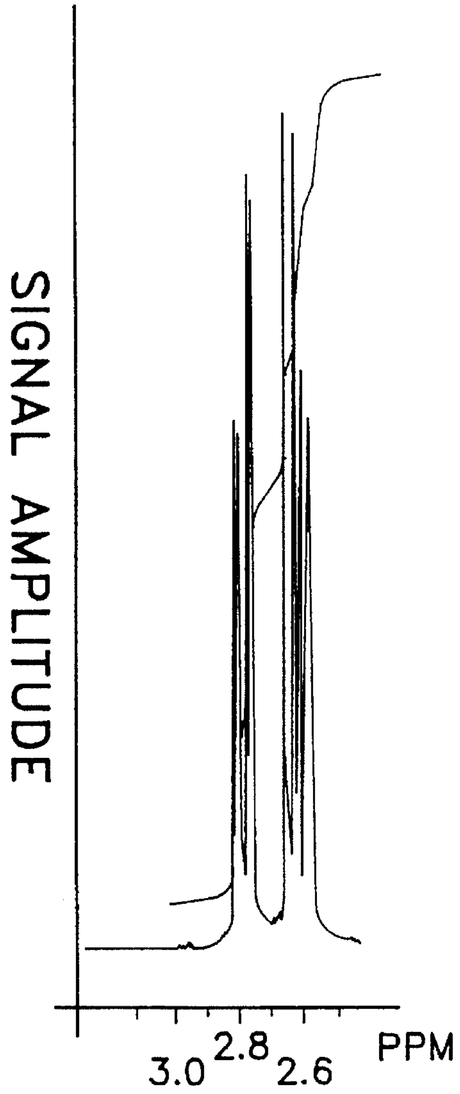
Figure 4D:
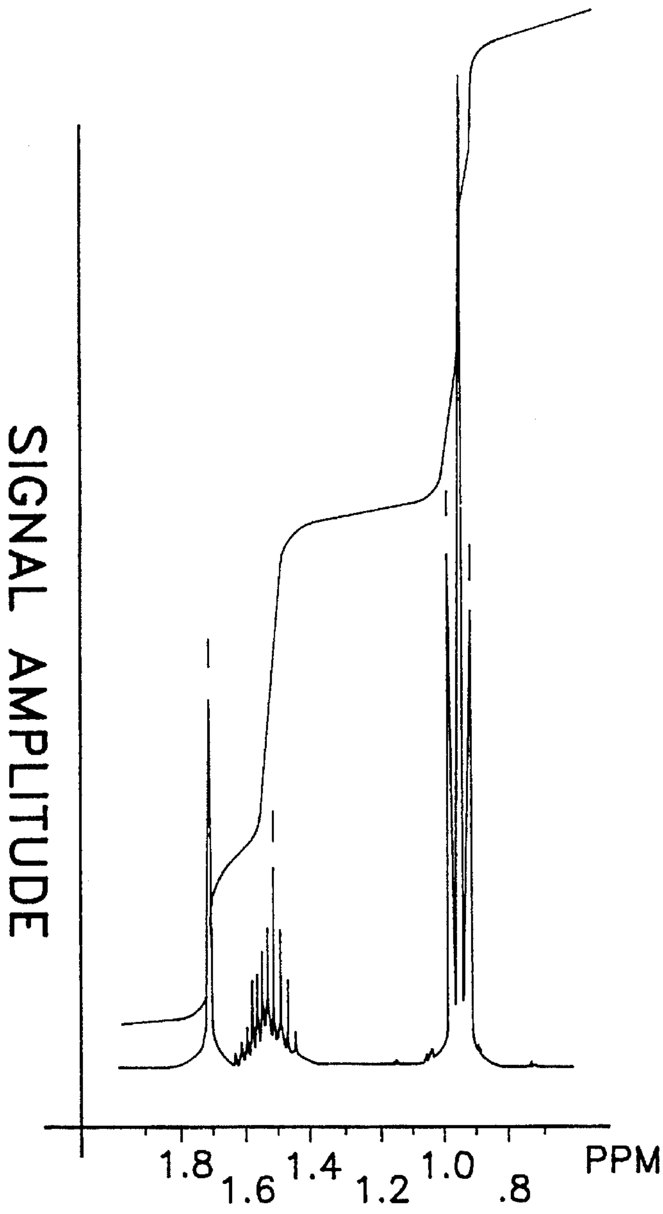

FIG. 4 is the NMR spectrum for the compound having the structure:

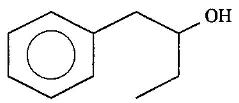

prepared according to Example II.

FIGS. 4A, 4B, 4C and 4D are enlargements of Sections "A", "B", "C" and "D" of the NMR spectrum of FIG. 4.

FIG. 5 is a partial side elevation view and partial sectional view of an apparatus for forming polymer pellets containing at least one of the phenyl alkanol derivatives of our invention.

FIG. 6 is a section taken along line 6—6 of FIG. 5.

DETAILED DESCRIPTION OF THE DRAWINGS

Figure 1:
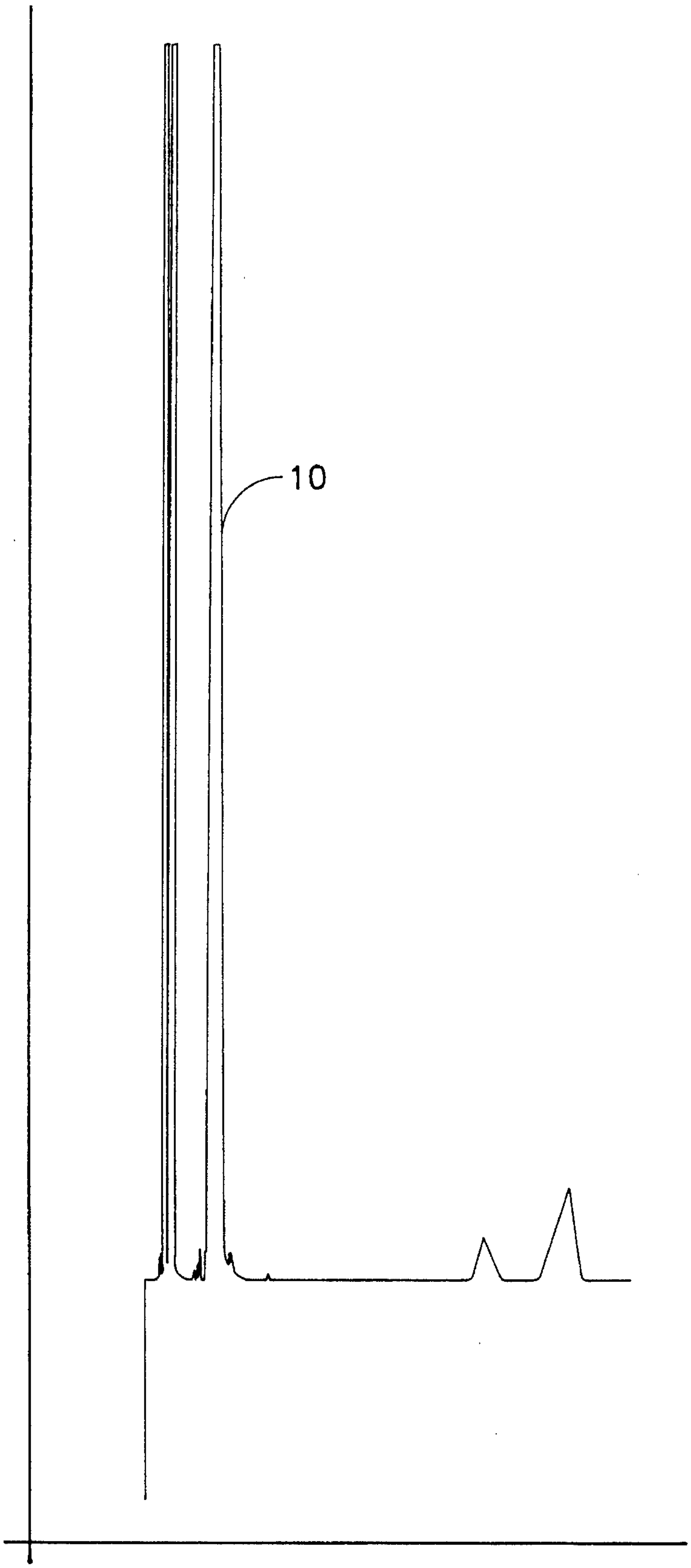
FIG. 1 is the GLC profile for the reaction product of Example I(A) containing the compound having the structure.

FIG. 1 is the GLC profile for the reaction product of Example I(A) containing the compound having the structure:

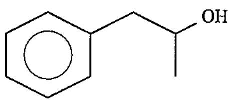

(conditions: SE-30 column programmed at 160° C. isothermal). The peak indicated by reference numeral 10 is the peak for the compound having the structure:

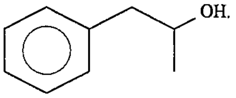

FIG. 2 is the GLC profile for the reaction product of Example I(B) (conditions: SE-30 column programmed at 160° C. isothermal). The peak indicated by reference numeral 20 is the peak for the compound having the structure:

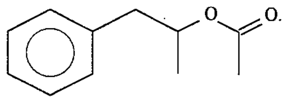

Referring to FIGS. 5 and 6, the apparatus used in producing polymeric fragrances containing one or more of the phenyl alkanol derivatives of our invention comprises a device for forming scented polyolefin (for example) pellets, which comprises a vat or container 212 into which a mixture of polyolefin such as polyethylene and an aromatic substance or scented material is placed (in this case at least one of the phenyl alkanol derivatives of our invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the phenyl alkanol derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the phenyl alkanol derivatives of our invention) are added to the polyolefin.

After the scent imparting material (e.g., a composition containing at least one of the phenyl alkanol derivatives of our invention) is added to the container 212, the mixture is stirred for a few minutes, for example, 5–15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter, the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., a mixture containing at least one of the phenyl alkanol derivatives of our invention) will continuously drop through orifices 234 downwardly from conduit 232. During this time, the temperature of the polymer (e.g., polyolefin) and aroma imparting material (e.g., a mixture containing at least one of the phenyl alkanol derivatives of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the phenyl alkanol derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

THE INVENTION

The present invention provides phenyl alkanol derivatives defined according to the generic structure:

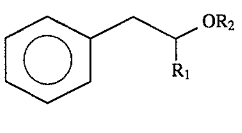

wherein $R_2$ is hydrogen or acetyl and $R_1$ is methyl or ethyl with the proviso that when $R_2$ is hydrogen, $R_1$ is ethyl and when $R_2$ is acetyl, $R_1$ is methyl as well as processes for utilizing such phenyl alkanol derivatives in perfumery.

The compositions of matter of our invention produced according to the processes disclosed in the instant specification are capable of augmenting, enhancing or providing strong, persistent, herbal, fruity, rose, ozoney, lilac, woody, mimosa, hyacinth, anise, jasmine and honey aromas with sweet, animalic, civet and fresh cut wood undertones to perfume compositions, colognes and perfumed articles (e.g., solid or liquid, anionic, cationic, nonionic or zwitterionic detergents, fabric softener articles, drier-added fabric softener articles, fabric softener compositions, cosmetic powders, hair preparations, perfumed polymers and the like).

The phenyl alkanol derivatives of our invention are known in the prior art, but their perfumery uses are not disclosed or inferred. The phenyl alkanol derivatives of our invention may be prepared by any one of a number of processes. Thus, a first process concerns reacting a benzyl Grignard reagent having the structure:

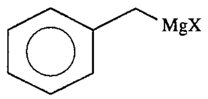

with an aldehyde having the structure:

wherein $R_1$ is defined, supra, according to the reaction:

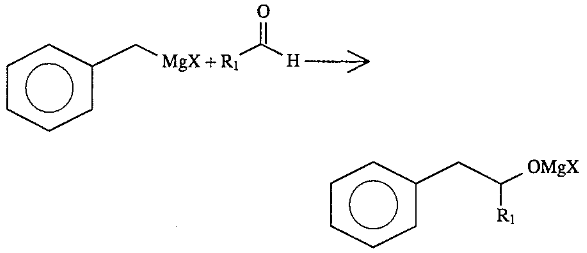

followed by a hydrolysis reaction:

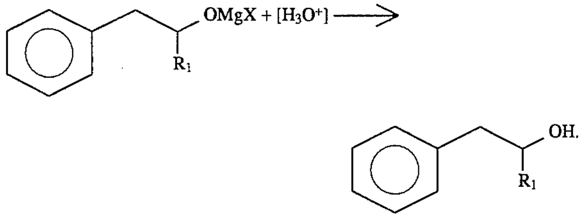

Alternatively, a benzyl Grignard reagent may be reacted with an epoxide defined according to the structure:

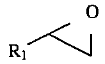

according to the reaction:

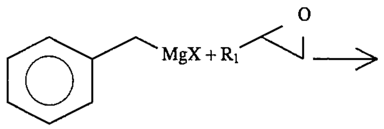

-continued

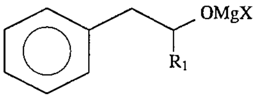

followed by the hydrolysis reaction:

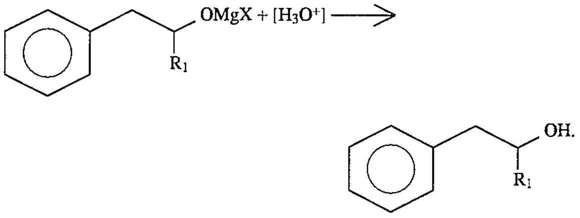

A third reaction sequence concerns reacting styrene oxide having the structure:

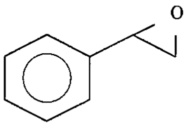

with a Grignard reagent according to the reaction:

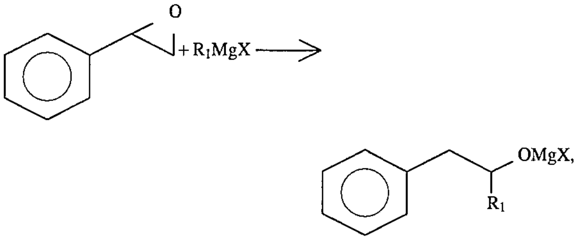

followed by the hydrolysis reaction:

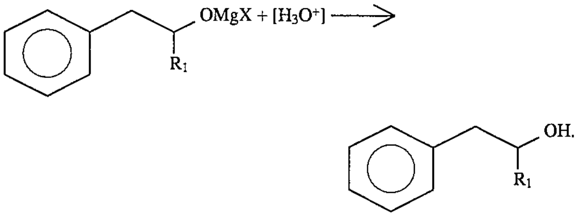

A fourth reaction sequence involves reacting phenyl acid aldehyde having the structure:

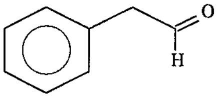

with the Grignard reagent having the structure:

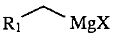

according to the reaction:

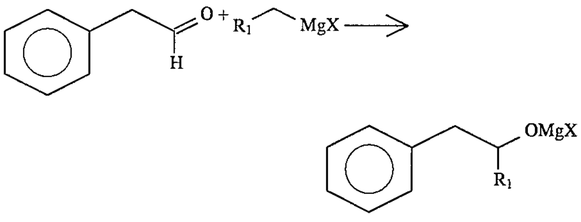

followed by the hydrolysis reaction:

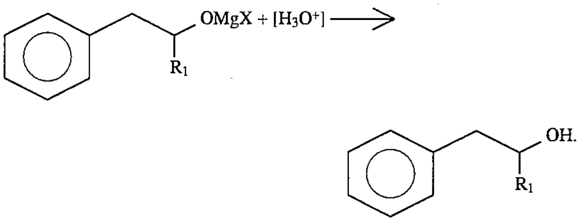

In the case of producing the ester, the resulting phenyl alkanol may then be reacted with an esterification reagent such as acetic anhydride according the reaction:

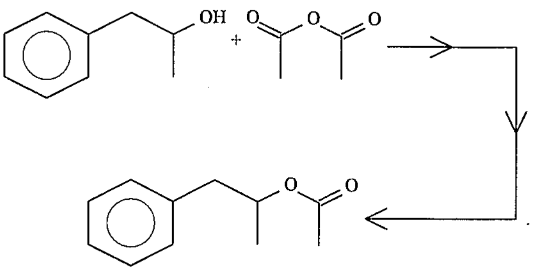

The conditions for each of the foregoing reactions are set forth in the prior art.

In each of the foregoing reaction sequences, X represents chloro or bromo.

Table I below sets forth the phenyl alkanol derivatives of our invention and their fragrance properties:

TABLE I

| Structure of Compound | Perfumery Property |
|---|---|
| The compound having the structure: 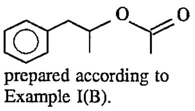 prepared according to Example I(B). | A herbal, fruity, rose, ozoney, lilac aroma with fresh cut wood and animalic undertones. |
| The compound having the structure: 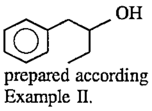 prepared according to Example II. | A woody, mimosa, hyacinth, lilac, anise, jasmine and honey aroma with sweet, animalic, civet undertones. |

One or more of the phenyl alkanol derivatives of our invention prepared in accordance with the processes set forth, supra, and one or more auxiliary perfume ingredients including, for example, alcohols other than the phenyl alkanols of our invention, aldehydes, ketones, terpenic hydrocarbons, nitriles, esters other than the ester of our invention, lactones, ethers, natural essential oils and synthetic essential oils may be admixed so that the combined odors of the individual components produce a pleasant and desired fragrance, particularly and preferably in the woody cologne and muguet fragrances. Such compositions usually contain:

(a) the main note or the "bouquet" or foundation stone of the invention;
(b) modifiers which round off and accompany the main note:
(c) fixatives which include odorous substances which lend a particular note to the perfume throughout all stages of evaporation and substances which retard evaporation; and
(d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the phenyl alkanol derivatives of our invention can be used to alter, modify or enhance the aroma characteristic of a perfume composition, for example, by utilizing or moderating the olfactory reaction contributed by another ingredient in the composition.

The amount of one or more of the phenyl alkanol derivatives of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of one or more of the phenyl alkanol derivatives of our invention or even less (e.g., 0.005%) can be used to impart, augment or enhance strong and persistent herbal, fruity, rose, ozoney, lilac, woody, mimosa, hyacinth, anise, jasmine and honey aromas with sweet, animalic, civet and fresh cut wood undertones to soaps, cosmetics, anionic, cationic, nonionic or zwitterionic detergents, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The phenyl alkanol derivatives of our invention prepared in accordance with a process as set forth, supra (taken alone or taken together with other ingredients in perfume compositions) as (an) olfactory component(s) in detergents and soaps, space odorants and deodorants, perfumes, colognes, toilet waters, bath preparations such as creams, deodorants, hand lotions and sun screens; powders, such as talcs, dusting powders, face powders, microporous "perfumed" slow release polymers and the like.

When used as (an) olfactory component(s) in perfumed articles, as little as 0.005% of one or more of the phenyl alkanol derivatives of our invention will suffice to impart, augment or enhance strong, persistent herbal, fruity, rose, ozoney, lilac, woody, mimosa, hyacinth, anise, jasmine and honey aromas with sweet, animalic, civet and fresh cut wood undertones. Generally, no more than 6% of at least one of the phenyl alkanol derivatives of our invention based on the ultimate end product is required in the perfumed article. Accordingly, the range of use of the phenyl alkanol derivatives of our invention in perfumed articles, per se, is from about 0.005% up to about 6% by weight based on the perfumed article.

In addition, the perfume composition or fragrance composition of our invention can contain a vehicle or carrier for one or more of the phenyl alkanol derivatives of our invention. The vehicle can be a liquid such as a non-toxic alcohol, e.g., ethyl alcohol, a non-toxic glycol, e.g., propylene glycol or the like. The carrier can be an absorbent solid such as a gum (e.g., gum arabic, guar gum or xanthan gum or combinations thereof) or components for encapsulating the composition (such as by coacervation) or using prepolymers such as urea-formaldehyde polymers which are able to form a urea-formaldehyde polymer capsule around a liquid perfume center.

It will thus be apparent that the phenyl alkanol derivatives of our invention can be utilized to alter, modify or enhance sensory properties particularly organoleptic properties such as fragrances of a wide variety of consumable materials.

The following Examples I and II set forth means for preparing the phenyl alkanol derivatives of our invention. The examples including and following Example III, infra, set forth illustrations of organoleptic utilities of the phenyl alkanol derivatives of our invention.

All parts and percentages given herein are by weight unless otherwise specified.

EXAMPLE I

PREPARATION OF ALPHA-METHYL PHENETHYL ALCOHOL ACETATE

Reactions:

Example I(A)

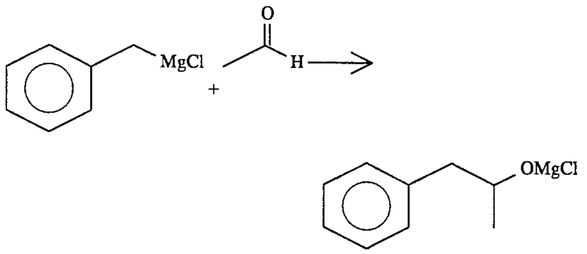

and

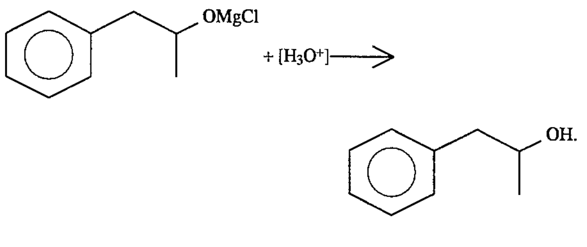

Example I(B)

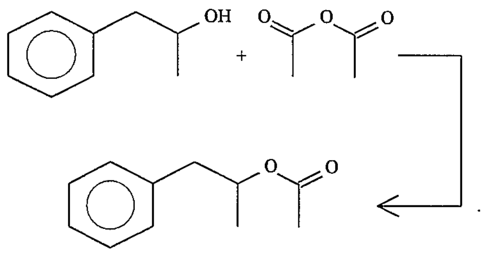

Into a 5 liter reaction vessel equipped with stirrer, thermometer, heating mantle and reflux condenser are placed the following ingredients:

162 grams of magnesium;

285 grams of tetrahydrofuran;

285 grams of toluene; and 45 grams of benzyl chloride.

Separately, a mixture containing 1,245 grams of toluene, 627 grams of tetrahydrofuran and 765 grams of benzyl chloride is prepared.

Over a period of one hour, while maintaining the reaction mass at 25°–30° C. with stirring, 30% of the toluene/tetrahydrofuran/benzyl chloride mixture is added to the reaction mass.

Over a period of one hour, 84 grams of acetaldehyde (6.45 moles) is added to the reaction mass.

Over a period of one hour, another third of the toluene/tetrahydrofuran/benzyl chloride mixture is added to the reaction mass while maintaining the reaction mass temperature at 25°–30° C.

Over a period of one hour, while maintaining the reaction mass temperature at 25°–30° C., 84 grams of additional acetaldehyde is added to the reaction mass.

With stirring, the final third of the toluene/tetrahydrofuran/benzyl chloride mixture is added to the reaction mass while maintaining the reaction mass temperature at 25°–30° C.

Over a period of an additional hour, an additional 84 grams of acetaldehyde is added to the reaction mass.

The reaction mass is then maintained for a period of one hour with stirring at 25°–30° C.

The reaction mass is then quenched with a mixture of 420 grams of acetic acid and 2 liters of water. The reaction mass is then further quenched with an additional 1 liter of dilute hydrochloric acid.

The reaction mass is then washed with two equal volumes of 10% aqueous sodium carbonate (pH=9).

The resulting reaction product is then fractionally distilled yielding the following fractions:

| Fraction Number | Vapor Temperature (°C.) | Liquid Temperature (°C.) | Vacuum mm/Hg. Pressure |
|---|---|---|---|
| 1 | 40/63 | 23/60 | 120 |
| 2 | 44 | 85 | 110 |
| 3 | 30 | 110 | 16 |
| 4 | 81 | 110 | 9 |
| 5 | 84 | 110 | 9 |
| 6 | 85 | 111 | 9 |
| 7 | 84 | 111 | 8 |
| 8 | 83 | 111 | 8 |
| 9 | 81 | 112 | 7 |
| 10 | 81 | 112 | 7 |

-continued

| Fraction Number | Vapor Temperature (°C.) | Liquid Temperature (°C.) | Vacuum mm/Hg. Pressure |
|---|---|---|---|
| 11 | 81 | 115 | 7 |
| 12 | 81 | 117 | 7 |
| 13 | 81 | 120 | 7 |
| 14 | 81 | 139 | 6.5 |
| 15 | 81 | 139 | 6.5 |
| 16 | 81 | 140 | 6.5 |
| 17 | 91 | 142 | 6.0 |

Fractions 3–13 are bulked.

Bulked distillation Fractions 3–13 are the compound having the structure:

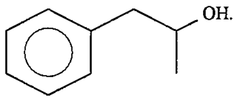

FIG. 1 is the GLC profile for the crude reaction product.

245 Grams of bulked distillation Fractions 3–13, the compound having the structure:

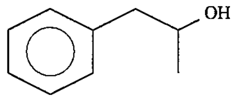

are placed in a 3 liter reaction vessel equipped with stirrer, thermometer and reflux condenser. 2.7 Moles (275 grams) of acetic anhydride is added to the reaction mass with stirring. 1,200 ml Toluene is then added to the reaction mass with stirring.

The reaction mass is heated to reflux and refluxed for a period of 8 hours at a temperature of between 121° and 124° C.

The reaction mass is then cooled to 80° C. The reaction mass is quenched with 400 ml water. The aqueous phase is separated from the organic phase.

The organic phase is washed twice with 300 ml of 10% aqueous sodium carbonate (pH=8.9).

The resulting reaction product is fractionally distilled yielding the following fractions:

| Fraction Number | Vapor Temperature (°C.) | Liquid Temperature (°C.) | Vacuum mm/Hg. Pressure |
|---|---|---|---|
| 1 | 23/42 | 23/105 | 30/120 |
| 2 | 97 | 103 | 5 |
| 3 | 98 | 102 | 5 |
| 4 | 98 | 103 | 5 |
| 5 | 98 | 103 | 5 |
| 6 | 98 | 103 | 5 |
| 7 | 99 | 103 | 5 |
| 8 | 99 | 103 | 5 |
| 9 | 99 | 103 | 5 |
| 10 | 99 | 104 | 5 |
| 11 | 99 | 106 | 5 |
| 12 | 99 | 108 | 5 |
| 13 | 100 | 112 | 5 |
| 14 | 94 | 145 | 2 |

Fractions 3–12 are bulked. Bulked distillation Fractions 3–12 are the compound having the structure:

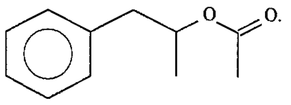

FIG. 2 is the GLC profile for the reaction product of the above example. The peak indicated by reference numeral 20 is the peak for the compound having the structure:

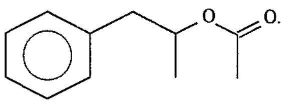

EXAMPLE II

PREPARATION OF BENZYL ETHYL CARBINOL

Reactions:

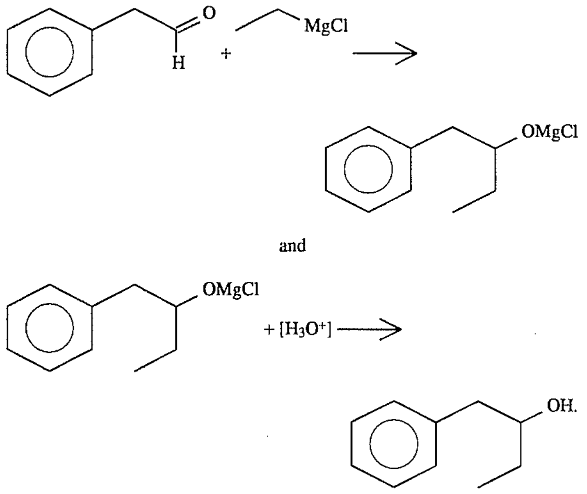

Into a 3 liter reaction vessel equipped with stirrer, thermometer, reflux condenser and heating mantle are charged 1,600 ml of 2 molar ethyl magnesium chloride (3.2 moles) (in diethyl ether).

Over a period of 2 hours, 360 grams (3.0 moles) of phenyl acid aldehyde having the structure:

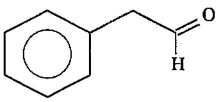

is added to the reaction mass while maintaining the reaction temperature at 50°–55° C.

The reaction mass is then maintained at 50°–55° C. for a period of 2 hours with stirring.

The reaction mass is then quenched with 2 liters of water and 210 grams of acetic acid. The organic phase is separated from the aqueous phase and the organic phase is washed with 500 ml 10% aqueous sodium carbonate (pH=8).

The organic phase is then fractionally distilled yielding the following fractions:

| Fraction Number | Vapor Temperature (°C.) | Liquid Temperature (°C.) | Vacuum mm/Hg. Pressure |
|---|---|---|---|
| 1 | 23/32 | 23/120 | 60/100 |
| 2 | 79 | 110 | 4 |
| 3 | 84 | 112 | 4 |
| 4 | 84 | 111 | 4 |
| 5 | 85 | 113 | 4 |
| 6 | 82 | 112 | 3 |
| 7 | 83 | 112 | 3.5 |
| 8 | 83 | 115 | 3.5 |
| 9 | 83 | 117 | 3.5 |
| 10 | 83 | 121 | 3.5 |
| 11 | 82 | 127 | 3 |
| 12 | 78 | 142 | 2 |
| 13 | 71 | 200 | <1 |

Fractions 6–11 are bulked.

Bulked distillation Fractions 6–11 are the compound having the structure:

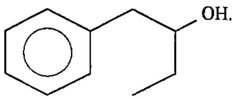

FIG. 3 is the GLC profile for the reaction product of Example II.

FIG. 4 is the NMR spectrum for the compound having the structure:

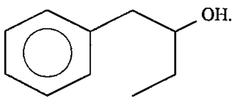

EXAMPLE III

PERFUME FORMULATIONS

The following woody cologne perfume formulations are prepared:

| | Parts by Weight | | |
|---|---|---|---|
| Ingredients | III(A) | III(B) | III(C) |
| Bergamot oil | 150 | 150 | 150 |
| Orange oil | 200 | 200 | 200 |
| Lemon oil | 50 | 50 | 50 |
| Eugenol | 10 | 10 | 10 |
| 4-(4-methyl-4-hydroxy amyl)-$\Delta^3$cyclohexane carboxaldehyde (LYRAL ® Trademark of International Flavors & Fragrances Inc. of New York, New York) | 40 | 40 | 40 |
| Ylang oil | 2 | 2 | 2 |
| Petigrain Paraguay | 10 | 10 | 10 |
| Gamma-Methyl ionone | 20 | 20 | 20 |
| Vetiver Venezuela | 18 | 18 | 18 |
| 3-Alpha-Methyl-dodecahydro-6,6.9a-trimethyl-napthol[2.1-b]furan | 5 | 5 | 5 |
| Product produced by the reaction of acetic anhydride, polyphosphoric acid and 1,5,9-trimethyl cyclododecatriene-1 5,9 according to the process of Example I of U.S. Pat. No. 3,718,698, the specification for which is incorporated by reference herein. | 50 | 50 | 50 |
| Octahydro-9,9-dimethyl-1,6-methano-naphthalene-1-[2H]-ol produced according to Example III of U.S. Pat. No. 3,996,169, the | 50 | 50 | 50 |

-continued

| Ingredients | Parts by Weight III(A) | III(B) | III(C) |
|---|---|---|---|
| specification for which is incorporated by reference herein. | | | |
| The compound having the structure: 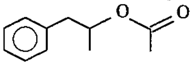 prepared according to Example I(B), supra. | 25 | 0 | 0 |
| The compound having the structure: 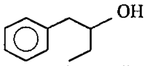 prepared according to Example II, supra. | 0 | 24 | 0 |
| A 50:50 (weight:weight) mixture of the compounds having the structures: 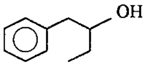 and 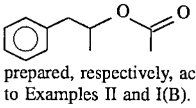 prepared, respectively, according to Examples II and I(B). | 0 | 0 | 12 |

The compound having the structure:

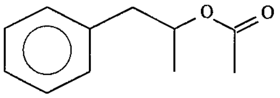

prepared according to Example I(B) imparts to this woody cologne formulation strong, persistent herbal, fruity, rose, ozoney, lilac, fresh cut wood and animalic undertones. Accordingly, the perfume composition of Example III(A) can be described as:

"a woody cologne aroma with strong, persistent herbal, fruity, rose, ozoney, lilac, fresh cut wood and animalic undertones".

The compound having the structure:

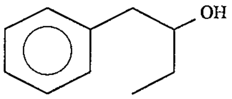

prepared according to Example II imparts to this woody cologne formulation strong, persistent woody, mimosa, hyacinth, lilac, anise, jasmine, honey, sweet, animalic, civet undertones. Accordingly, the perfume composition of Example III(B) can be described as:

"a woody cologne aroma with strong, persistent woody, mimosa, hyacinth, lilac, anise, jasmine, honey, sweet, animalic and civet undertones".

The combination of the compounds having the structures:

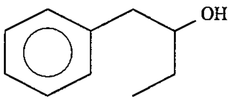

-continued and

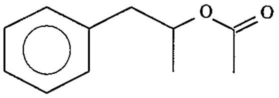

imparts to this woody cologne formulation strong, persistent herbal, fruity, rose, ozoney, lilac, woody, mimosa, hyacinth, anise, jasmine, honey, sweet, animalic, civet and fresh cut wood undertones. Accordingly, the perfume composition of Example III(C) can be described as a:

"a woody cologne aroma with strong, persistent herbal, fruity, rose, ozoney, lilac, woody, mimosa, hyacinth, anise, jasmine, honey, sweet, animalic, civet and fresh cut wood undertones".

EXAMPLE IV

PREPARATION OF COSMETIC POWDER COMPOSITION

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 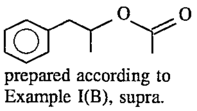 prepared according to Example I(B), supra. | A herbal, fruity, rose, ozoney and lilac aroma with fresh cut wood and animalic undertones. |
| The compound having the structure: 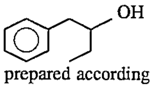 prepared according Example II. | A woody, mimosa, hyacinth, lilac, anise, jasmine and honey aroma with sweet, animalic and civet undertones. |
| The perfume composition of Example III(A). | A woody cologne aroma with strong, persistent herbal, fruity, rose, ozoney, lilac, fresh cut wood and animalic undertones. |
| The perfume composition of Example III(B). | A woody cologne aroma with strong, persistent woody, mimosa, hyacinth, lilac, anise, jasmine, honey, sweet, animalic and civet undertones. |
| The perfume composition of Example III(C). | A woody cologne aroma with strong, persistent herbal, fruity, rose, ozoney, lilac, woody, mimosa, hyacinth, anise, jasmine, honey, sweet, animalic, civet and fresh cut wood undertones. |

EXAMPLE V

PERFUMED LIQUID DETERGENTS

Concentrated liquid detergents (Lysine salt of n-dodecybenzene sulfonic acid as more specifically described in U.S. Pat. No. 3,948,818 issued on Apr. 6, 1976 incorporated by reference herein) with aroma nuances as set forth in Table II of Example IV are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentrations of substances as set forth in Table II of Example IV.

EXAMPLE VI

PREPARATION OF COLOGNE AND HANDKERCHIEF PERFUMES

Compositions as set forth in Table II of Example IV are incorporated into colognes at concentrations of 2.0%, 2.5%, 3.0%, 3.5%, 4.0% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example IV are imparted to the colognes and to the handkerchief perfumes at all levels indicated.

EXAMPLE VII

PREPARATION OF SOAP COMPOSITION

100 Grams of soap chips [per sample] (IVORY® produced by the Procter & Gamble Company of Cincinnati, Ohio) are each mixed with 1 gram samples of substances as set forth in Table II of Example IV until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example IV.

EXAMPLE VIII

PREPARATION OF SOLID DETERGENT COMPOSITIONS

Detergents are prepared using the following ingredients according to Example I of Canadian Patent No. 1,007,948 (incorporated by reference herein):

| Ingredients | Percent by Weight |
|---|---|
| NEODOL ® 45-11 (a $C_{12}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS;
   22% isopropyl alcohol;
   20% antistatic agent; and
   1% of one of the substances as set forth in Table II of Example IV, supra.

Fabric softening compositions prepared according to Example I at column 15 of U.S. Pat. No. 3,632,396 having the aroma characteristics as set forth in Table II of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added softener non-woven fabrics and these aroma characteristics are described in Table II of Example IV, supra.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% of food grade ethanol. 8.0 Grams of the polymer is dissolved in the alcohol. The following ingredients are added to the PVP/VA alcoholic solution:

| Ingredients | Percent by Weight |
|---|---|
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example IV, supra | 0.10 |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stephan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example IV is added to the mixture. The resulting mixture is cooled to 40° C. and blending is carried out for an additional one hour in each case. At the end of this blending period, the resulting material has a pleasant fragrance as indicated in Table II of Example IV.

What is claimed is:

1. A process for augmenting, enhancing or imparting an aroma in or to a consumable material selected from the group consisting of perfume compositions, perfumed articles and colognes comprising the step of intimately admixing with said consumable material an aroma augmenting, enhancing or imparting quantity and concentration of a phenyl alkanol derivative defined according to the structure:

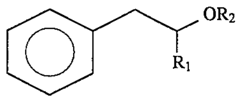

wherein $R_2$ is selected from the group consisting of hydrogen and acetyl and $R_1$ is selected from the group consisting of methyl and ethyl with the proviso that when $R_2$ is hydrogen, $R_1$ is ethyl and when $R_2$ is acetyl, $R_1$ is methyl.

2. The process of claim 1 wherein the phenyl alkanol derivative has the structure:

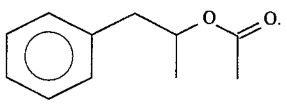

3. The process of claim 1 wherein the phenyl alkanol derivative has the structure:

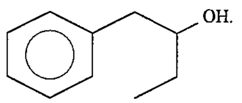

4. The process of claim 1 wherein the consumable material is a perfume composition.

5. The process of claim 1 wherein the consumable material is a perfumed article.

6. The process of claim 1 wherein the consumable material is a perfumed polymer.

7. A consumable material selected from the group consisting of perfume compositions, perfumed articles and colognes comprising a consumable material base and intimately admixed therewith an aroma augmenting, enhancing or imparting quantity and concentration of a phenyl alkanol derivative defined according to the structure:

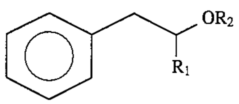

wherein $R_2$ is selected from the group consisting of hydrogen and acetyl and $R_1$ is selected from the group consisting of methyl and ethyl with the proviso that when $R_2$ is hydrogen, $R_1$ is ethyl and when $R_2$ is acetyl, $R_1$ is methyl.

8. The consumable material of claim 7 wherein the consumable material is a perfume composition.

9. The consumable material of claim 7 wherein the consumable material is a perfumed article.

10. The consumable material of claim 7 wherein the consumable material is a cologne consisting of water, alcohol and an aroma augmenting, enhancing or imparting quantity and concentration of a compound defined according to the structure:

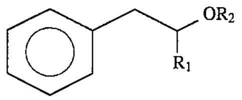

wherein $R_2$ is selected from the group consisting of hydrogen and acetyl and $R_1$ is selected from the group consisting of methyl and ethyl with the proviso that when $R_2$ is hydrogen, $R_1$ is ethyl and when $R_2$ is acetyl, $R_1$ is methyl.

11. The consumable material of claim 7 wherein the consumable material is a perfumed microporous polymer and the compound defined according to the structure:

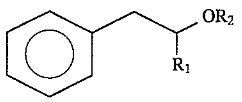

is contained within the interstices of said microporous polymer.

* * * * *